(12) United States Patent
Zyromski

(10) Patent No.: US 6,831,269 B2
(45) Date of Patent: Dec. 14, 2004

(54) LESION PHANTOMS WITH NO INNER COLD ENCAPSULATION

(75) Inventor: Kristiana E. Zyromski, Frazier Park, CA (US)

(73) Assignee: Iso-Science Laboratories, Inc., Valencia, CA (US)

( * ) Notice: Subject to any disclaimer, the term of this patent is extended or adjusted under 35 U.S.C. 154(b) by 20 days.

(21) Appl. No.: 10/278,412

(22) Filed: Oct. 22, 2002

(65) Prior Publication Data

US 2004/0076258 A1 Apr. 22, 2004

(51) Int. Cl.⁷ ................................................ G09B 23/28
(52) U.S. Cl. ........................ 250/252.1; 250/363.01
(58) Field of Search ........................ 250/252.1, 363.01, 250/363.09, 505.1; 600/458, 437, 439; 424/9.51, 9.52, 450; 378/18, 207

(56) References Cited

U.S. PATENT DOCUMENTS

| 4,014,109 A | | 3/1977 | Schramm | |
|---|---|---|---|---|
| 4,055,771 A | * | 10/1977 | Goodenough et al. | ........ 378/18 |
| 4,280,047 A | * | 7/1981 | Enos | ........................ 250/252.1 |
| 4,331,869 A | | 5/1982 | Rollo | |
| 4,460,832 A | * | 7/1984 | Bigham | .................... 250/505.1 |
| 4,499,375 A | * | 2/1985 | Jaszczak | .................. 250/252.1 |
| 5,633,499 A | | 5/1997 | Lim et al. | |
| 5,954,513 A | * | 9/1999 | Miller | ......................... 434/262 |
| 6,207,952 B1 | * | 3/2001 | Kan et al. | ................. 250/252.1 |
| 6,362,471 B1 | * | 3/2002 | Spitz et al. | ............... 250/252.1 |
| 6,490,336 B1 | * | 12/2002 | Suess et al. | ................... 378/18 |
| 6,668,073 B1 | * | 12/2003 | Robar et al. | ................ 382/128 |
| 2004/0021065 A1 | * | 2/2004 | Weber | ...................... 250/252.1 |

FOREIGN PATENT DOCUMENTS

WO     WO 00/12007     3/2000

* cited by examiner

Primary Examiner—Constantine Hannaher
Assistant Examiner—Otilia Gabor
(74) Attorney, Agent, or Firm—Christie, Parker & Hale, LLP

(57) ABSTRACT

A lesion phantom with no inner cold encapsulation. The phantom has a plurality of lesion analogues formed without any encapsulation by a dissimilar material and formed of a matrix of solidified material. A background matrix into which at least one radionuclide is dispersed to form a background level of radioactivity. The background matrix is placed in a container. The background level of radioactivity of the background matrix is different than that of the level of radioactivity of the plurality of lesion analogues.

32 Claims, 6 Drawing Sheets

LESION PHANTOMS WITH NO INNER COLD ENCAPSULATION

BACKGROUND OF THE INVENTION

The invention relates to the field of medical imaging devices, and more particular to lesion phantoms with no inner cold encapsulation for use as a calibration or reference source for medical imaging detectors such as gamma cameras, single-photon-emission computed tomography (SPECT) scanners and positron emission tomography (PET) scanners.

Gamma cameras, SPECT scanners and PET scanners are highly sensitive devices that need routine calibration for optimal performance. One straightforward way to calibrate a gamma camera, a SPECT or a PET scanner and determine what resolution, image contrast, slice thickness, etc. the device is capable of detecting is to use a phantom with known characteristics, such as the size, radioactive activity level agents and structures, and other features the user is interested in measuring. One cannot reliably and consistently determine these parameters in a patient. Use of a phantom provides numerous advantages, including providing a standardized test procedure, providing a way to allow comparison of results from month to month, permitting users to compare one scanner to another scanner, permitting a user to decide on clinical protocols for acquisition and processing ahead of time, and lastly, providing a way to permit a user to practice patient setup and image processing techniques. Others have provided medical imaging phantoms which include vessels (which have a vessel wall thickness) that are to be filled with a radioactive ("hot") tracer solution to form a hot spot. Because of scanning requirements, the radioactive solutions placed in these vessels are typically selected to comprise the same medical radioactive isotope(s) (which have relatively very short half lives) that will be used to image an animal or human patient, these prior art phantoms must generally be prepared shortly before use in calibrating a scanner. In turn, these radioactive tracer solution filled vessels are placed in containers of background liquid (e.g. with a lower level of radioactivity ("warm")). This is time consuming as the user must mix the radioactive solution and then fill the separate vessels prior to use. Another big problem with these prior phantoms is that the walls of the vessels are cold (i.e. non-radioactive.) During imaging, the cold layers around the hot liquid cause an averaging or washing out in the image, which results in a non-quantitative picture of the hot spot. This can be particularly problematic with small sized vessels, which will have small hot spots.

It would therefore be beneficial to have a phantom that does not need to be filled with radioactive tracer solution prior to each use and which also does not have a cold layer between the hot (or cold) spot and the warm background.

SUMMARY OF THE INVENTION

The invention provides permanent lesion phantoms in which lesion phantoms with no inner cold encapsulation are placed in a radioactive warm background. The lesion phantom is a sealed radioactive source designed to be used as a calibration or reference source for medical imaging detectors such as gamma cameras, SPECT scanners, and PET scanners.

The phantom consists of an outer capsule loaded with a solid radioactive matrix material such as epoxy at a given "background" activity level, with regions ("lesion analogues" or "hot" or "cold" spots) of higher or lower radioactive activity density imbedded in the background-level material. There is no nonradioactive ("cold") encapsulation or material between the lesion analogues and the background-level material.

The phantom can have any number of shapes, such as a cylinder, a box, or anthropomorphic shapes such as heart, breast, torso, brain, thyroid mimics, and other organs and structures.

For phantoms intended for medical imaging, the matrix material can be chosen to be of water- or tissue-equivalent density. Other densities could be used to meet the needs of other applications. The lesion analogue and the background matrix can be formed from material including but not limited to resins, urethanes, silicones, polymer gels, cements, and castable ceramics. It is preferably that the matrix, once formed, be a non-liquid.

The radionuclide used is a known calibrator for the detector system the source is to be used with, or has radiation energies similar to radionuclides used with this detector system. These include, but are not limited to Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95, with Ba-133, Co-57, Ge-68, Na-22, Gd-153, Cs-137 and Se-75 being particularly good nuclides. Furthermore, combinations of two or more radionuclides can be used.

The lesion analogues may vary in size from 0.1 mm$^3$ (or smaller) to 100 cm$^3$ (or larger), depending on the intended purpose of the particular phantom configuration. For example, the best present gamma camera have a resolution of about 1 millimeter or less, and with advances, resolutions are regularly improving. Lesion analogue activity density relative to the background activity density may range from zero (a completely nonradioactive lesion analogue) to 100 times or more background activity density. A typical "hot-spot" phantom would have three to six lesion analogues varying in size from slightly smaller than the detector resolution limit to a size easily seen by the detector, with hot spot activity density being about ten times the background activity density. A typical "cold spot" or "defect" phantom would have three to six lesions varying in size from slightly smaller than the detector resolution limit to a size easily seen by the detector, with cold spot activity densities of, for example, 75%, 50%, 25% of background activity density, and a cold, or nonradioactive, lesion analogue.

The intended use of these lesion phantoms is for image registration, quality control, resolution and contrast measurement, and qualitative and/or quantitative scatter and attenuation measurements for medical imaging detectors. Other uses and configurations may be possible for non-medical imaging applications.

DETAILED DESCRIPTION OF THE INVENTION

Figure 1:
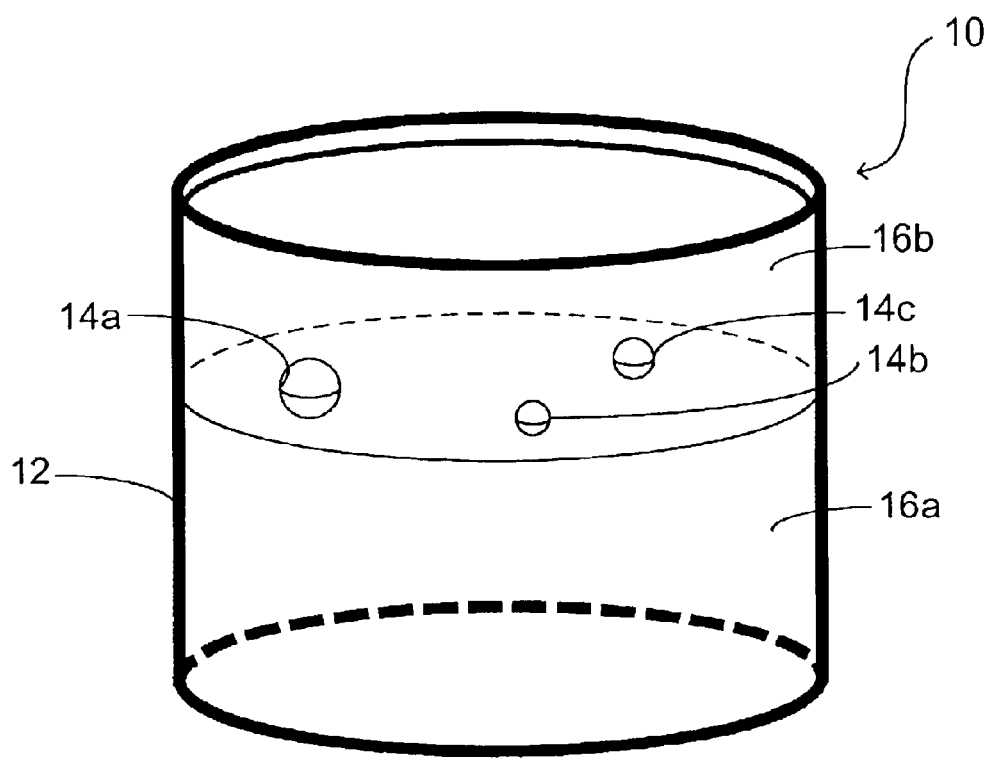
FIG. 1 is a perspective view of an embodiment of a completed lesion phantom of the invention.
Figure 2:
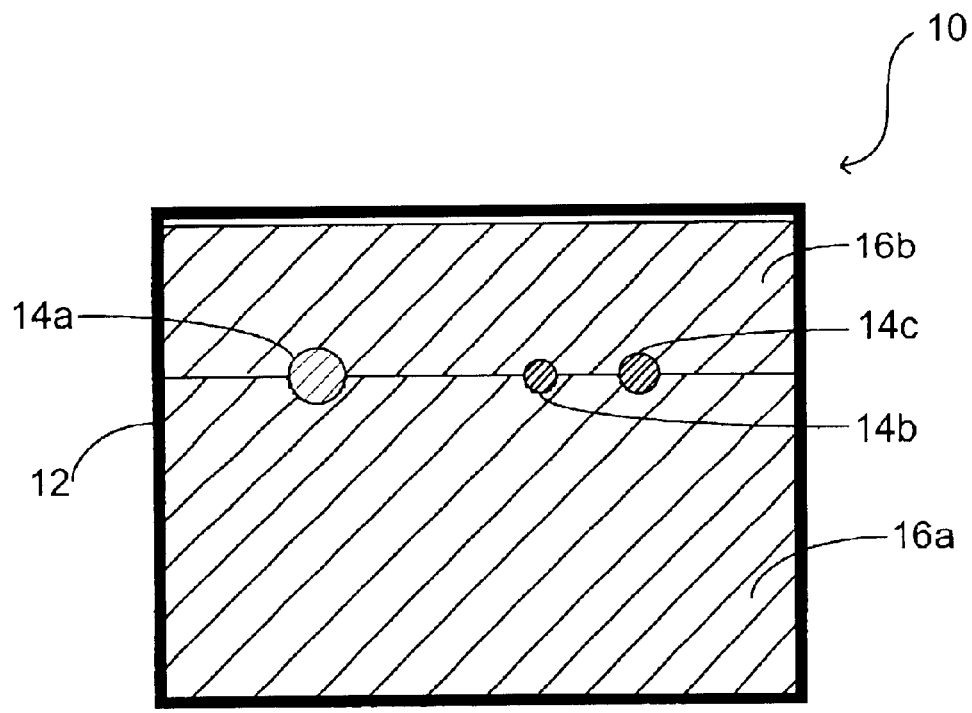
FIG. 2 is a cross sectional view of the lesion phantom of FIG. 1.

Referring to FIGS. 1 and 2, there is shown a perspective view and a cross section view of a first lesion phantom with no inner cold encapsulation 10 of the invention. Phantom 10 has a container portion 12, with at least one and preferably a plurality of different lesion analogues 14a, 14b, 14c, etc. Lesion analogues 14a, 14b, 14c are located in a volume of material 16a and 16b that has a different level of radioactivity to provide either a colder or hotter background than lesion analogues 14a, 14b, 14c. The material can comprise a resin, a urethane, a silicone, a polymer gel, a cement, a castable ceramic, or other material to which one or more different radioactive isotopes have been added. It is preferably that the matrix, once formed, be a non-liquid. In cases where cold lesion analogues 14a, 14b, 14c are desired, no radionuclides are added to the material used to form the cold lesion analogues 14a, 14b, 14c. The material (whether hot or cold) is then cast into desired shapes and sizes. For radioactive lesion analogues, one or more desired radionuclides are dispersed into the material, placed in molds, and at least partially cured into solid bodies. The radionuclides used can be known calibrators for the detector system the source is to be used with, or can have radiation energies similar to the radionuclides used with the selected detector systems. These include, but are not limited to Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95, with Ba-133, Co-57, Ge-68, Na-22, Gd-153, Cs-137 and Se-75 being particularly good nuclides.

Furthermore, combinations of two or more radionuclides can be used. These radionuclides can be blended in a matrix of epoxy resin or other materials, such as urethanes, silicones, cements, castable ceramics, or any number of other materials. Since the cured resin solid bodies (or other materials) will generally retain their own shape, there is no need for containment vessels with non-radioactive walls. Accordingly, there will be no nonradioactive envelope surrounding lesion analogues which would show up as a cold layer during imaging. Although lesion analogues 14a, 14b, 14c are shown as generally spherical bodies, they can be shaped and sized as desired, such as to mimic tumors, cold areas that might show up on heart scans that indicate areas of tissue death, and other desirable shapes and sizes.

Figure 3:
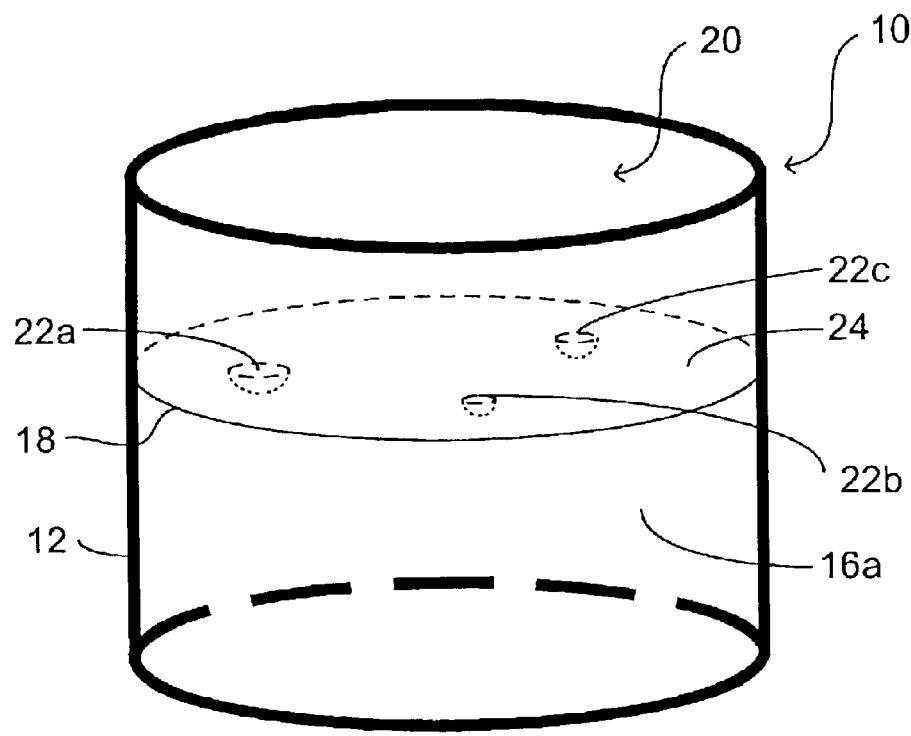
FIG. 3 is a perspective view of a partially assembled lesion phantom of FIG. 1 wherein a first layer of background matrix with recesses is formed.
Figure 4:
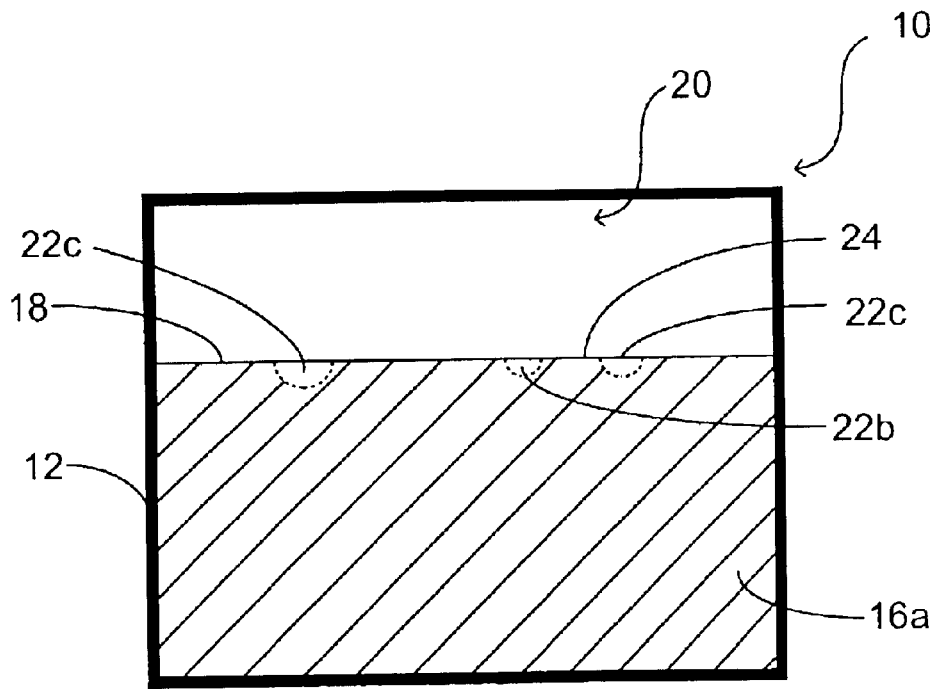
FIG. 4 is a cross sectional view of the partially assembled lesion phantom of FIG. 3.

One practical method by which lesion phantom 10 can be made is depicted in FIGS. 3–8. FIGS. 3 and 4 show a lower resin layer 16a, with a low level of radioactivity to provide a warm background, which is placed in container 12 to a desired level 18. Container 12 may have an open top 20. Recesses 22a, 22b, and 22c, etc. can be formed into the upper surface 24 of lower resin layer 16a, such as by molding. Recesses 22a, 22b, and 22c are preferably contoured to closely receive a lower portion of hot spot markers 14a, 14b and 14c, respectively.

Figure 5:
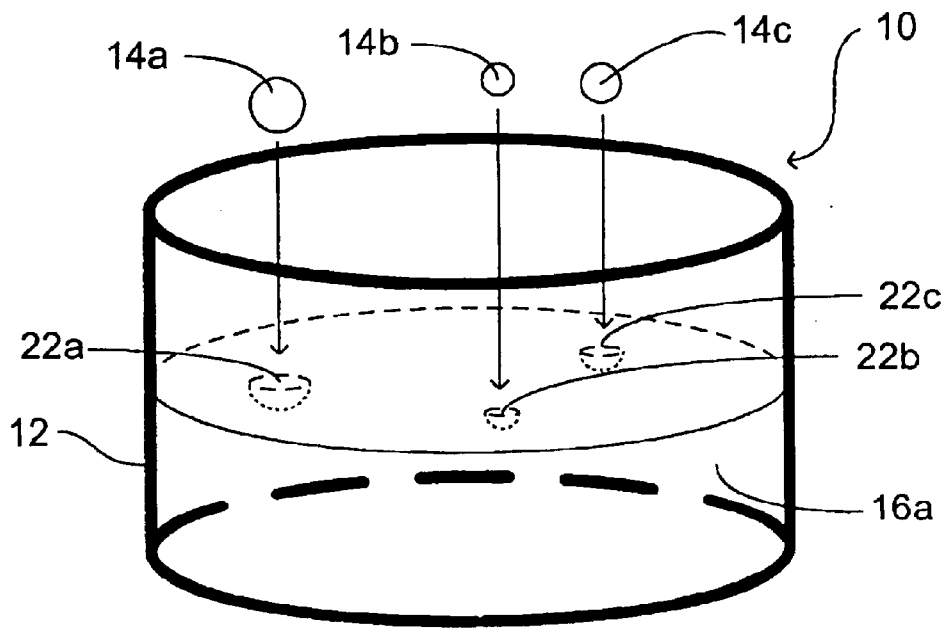
FIG. 5 is a perspective view of a partially assembled lesion phantom of FIG. 1 wherein a plurality of lesion analogues are be ready to be placed in the recesses of the first layer of background matrix.
Figure 6:
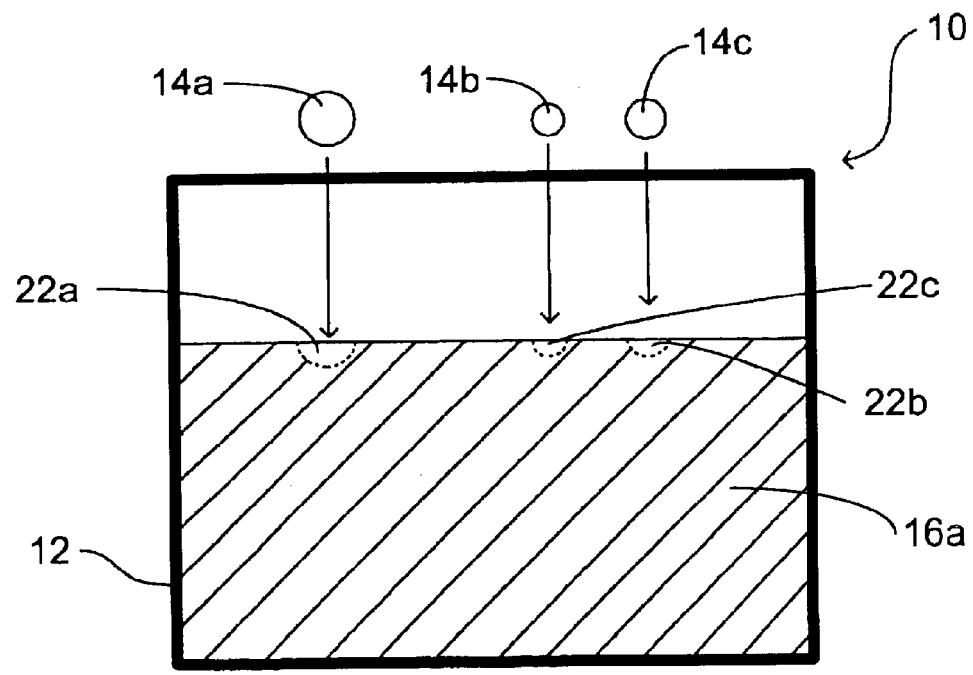
FIG. 6 is a cross sectional view of the partially assembled lesion phantom of FIG. 5.

FIGS. 5 and 6 show hot lesion analogues 14a, 14b and 14c to be placed into recesses 22a, 22b and 22c, respectively, on resin layer 16a, through open top 20 of container 12.

Figure 7:
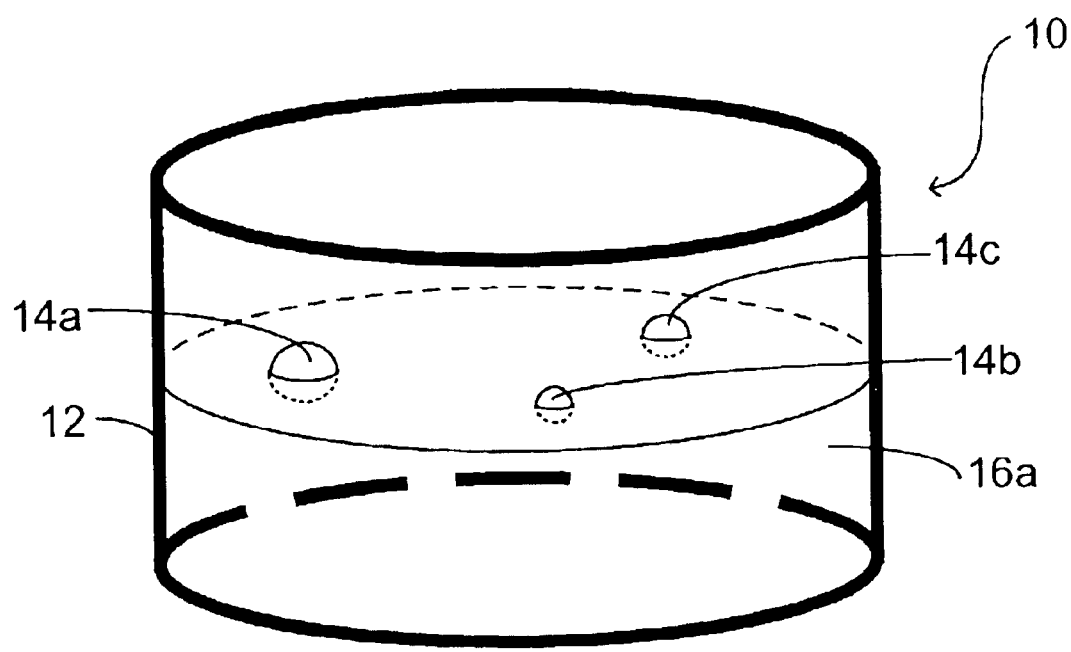
FIG. 7 is a perspective view of a partially assembled lesion phantom of FIG. 1 wherein a plurality of lesion analogues are placed in the recesses of the first layer of background matrix.
Figure 8:
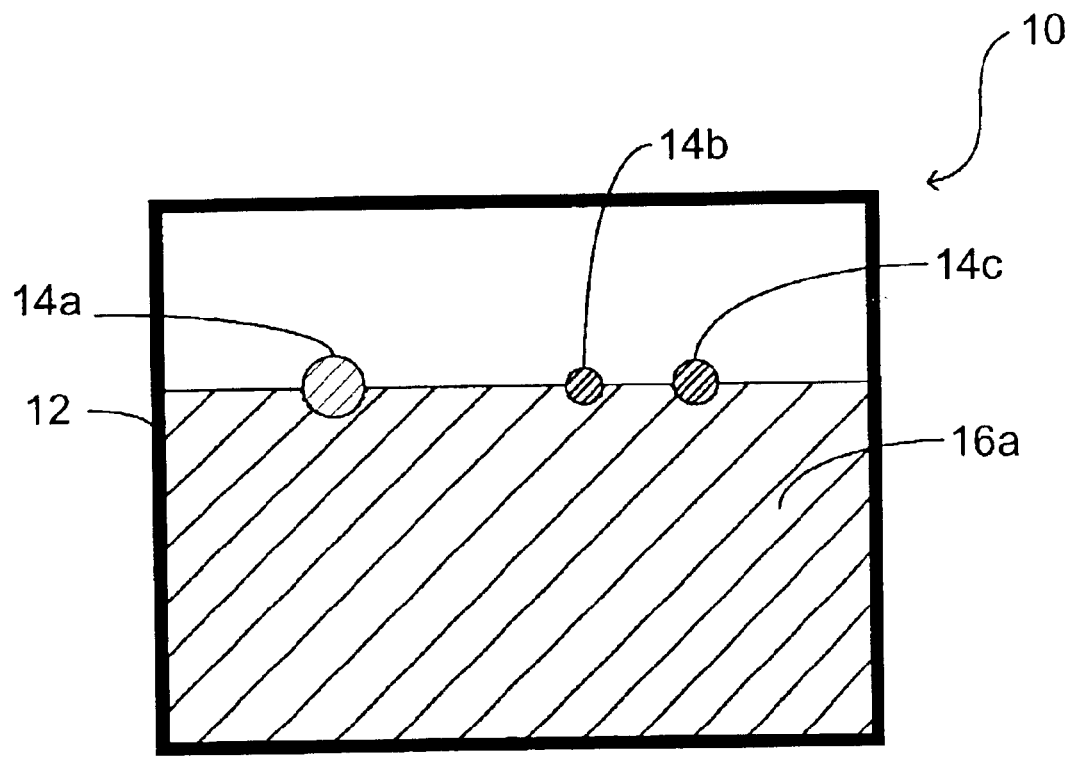
FIG. 8 is a cross sectional view of the partially assembled lesion phantom of FIG. 7.

FIGS. 7 and 8 show lesion analogue markers 14a, 14b and 14c after being placed into recesses 22a, 22b and 22c, respectively, on resin layer 16a.

Turning back to FIGS. 1 and 2, the completed lesion phantom is shown, with second layer of radioactive resin 16b poured over first layer 16a. Since differences in the level of radioactivity between first layer 16a and second layer 16b might show up on a scan, it is preferable to ensure that the characteristics of first layer 16a and second layer 16b (e.g. same radioactivity and density) are as close as possible. One way to accomplish this is to make a single batch of resin or other material with the radionuclide mixed in, and to form first layer 16a with recesses 22a, 22b, and 22c, that are at least partially sized to fit lesion analogues markers. It is preferably that the material, once formed, be a non-liquid. The unused portion is reserved in an uncured state for the second layer. Thereafter, first layer is cured (e.g. by heat.) Next, lesion analogues markers 14a, 14b and 14c are positioned in the empty locations on the first layer 16a. Lastly, the uncured batch of radioactive resin or other material reserved will be disposed over lesion analogues markers 14a, 14b and 14c as second layer 16b, and cured in place. Following these steps, even though layers 16a and 16b are separately formed, they will, on a scanner, have the appearance of a unitary and undivided structure.

Figure 9:
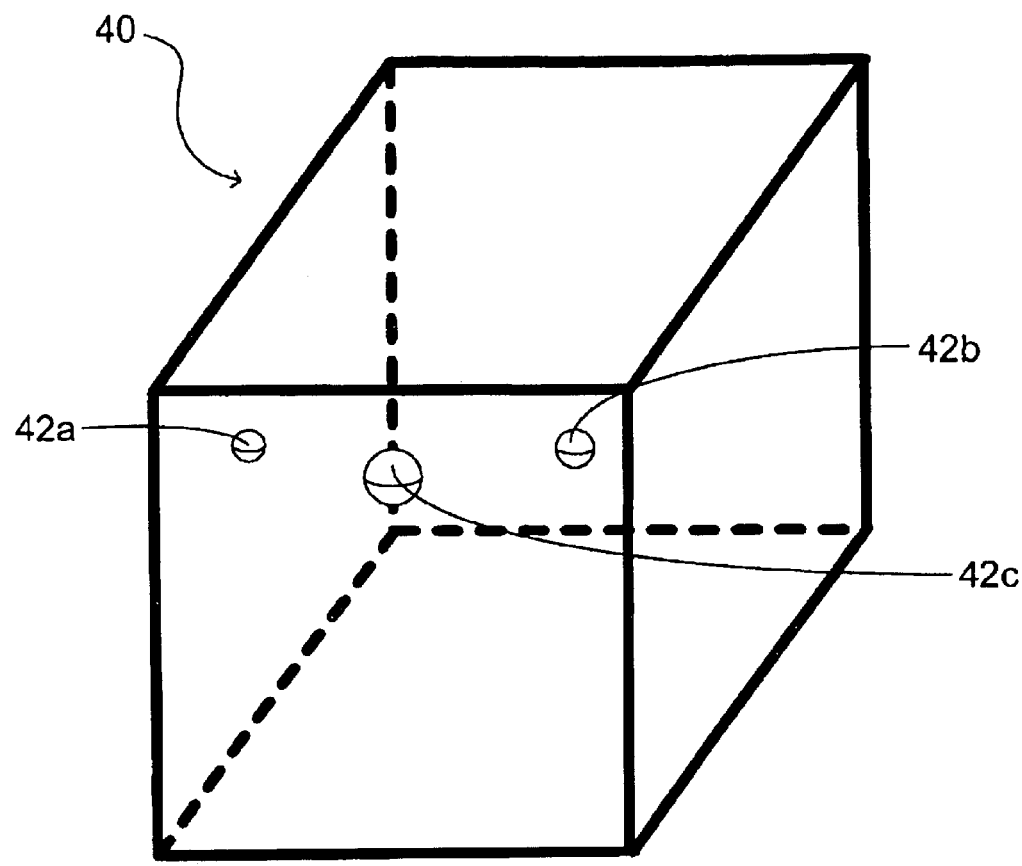
FIG. 9 is a perspective view of another embodiment of a completed lesion phantom of the invention.
Figure 10:
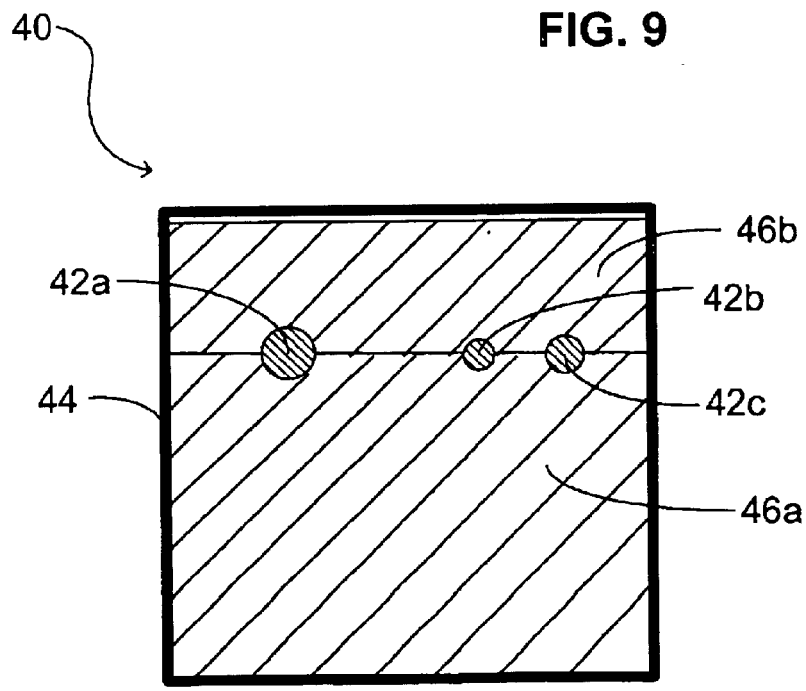
FIG. 10 is a cross sectional view of the lesion phantom of FIG. 9.

Referring to FIGS. 9 and 10, there is shown a side view of an embodiment of another lesion phantom 40 in the shape of a box. A plurality of lesion analogues 42a, 42b and 42c are shown positioned in a box-shaped container 44. Lesion analogues 42a, 42b and 42c are situated in layers 44a and 44b of resin that preferably has a background level of radioactivity. Lesion analogues 42a, 42b and 42c are constructed as in the first embodiment described with reference to FIGS. 1–8, and likewise, have no nonradioactive layer of material formed around their outer surfaces.

Figure 11:
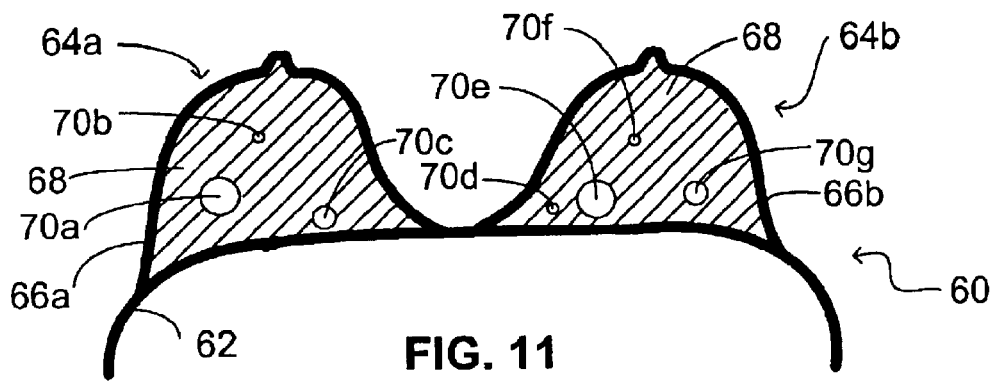
FIG. 11 is a cross sectional view of an anthropomorphic lesion phantom configuration.

Turning to FIG. 11, there is shown a side view of an exemplary anthropomorphic lesion phantom configuration 60 in the form of a portion of chest wall and two breasts in the prone orientation. Other anthropomorphic lesion phantom configuration, such as heart, brain, torso, thyroid, abdomen, etc., can be provided. Lesion phantom configuration comprises a chest wall portion 62 and two breast analogue portions 64a and 64b. Breast analogue portions 64a and 64b have outer walls 66a and 66b, and are filled with a filler matrix 68 that preferably has a background level of radioactivity. Filler 68 can comprise a matrix of epoxy resin or other materials, such as urethanes, silicones, castable ceramics, or any number of other materials, with at least one type of radionuclide dispersed therethrough. For phantoms intended for medical imaging, the filler matrix material can be chosen to be of water- or tissue-equivalent density. Other densities could be used to meet the needs of other applications. For anthropomorphic lesion phantom configuration, it is desirable to use a filler that have similar characteristics as the tissue being scanned. Contained within the filler are at least one and preferably a plurality of lesion analogues 70a, 70b, 70c, 70d, 70e, 70f and 70g. Lesion analogues 70a, 70b, 70c, 70d, 70e, 70f and 70g are preferably constructed as in the first embodiment described with reference to FIGS. 1–8, and likewise, have no nonradioactive layer of material formed around their outer surfaces.

To permit the greatest utilization in a variety of scanners, including dual CT/PET scanners, and CT scanners used in conjunction with PET and/or SPECT scanners, the lesion phantoms can also include features that can be imaged not only by a PET and/or SPECT scanner, but also by a CT scanner. This can be accomplished by locating radiopaque objects in or on the phantom that are detectable by CT scanning in addition to the above noted lesion analogues that show up in the PET and SPECT scans. The radiopaque objects can preferably be comprised of natural or artificial materials that have radiopaque characteristics similar to animal tissue (such as bone). Different sizes and configures for the phantoms can be provided, such as phantoms that would mimic small animal anatomy as well as larger animal and human anatomy.

Figure 12:
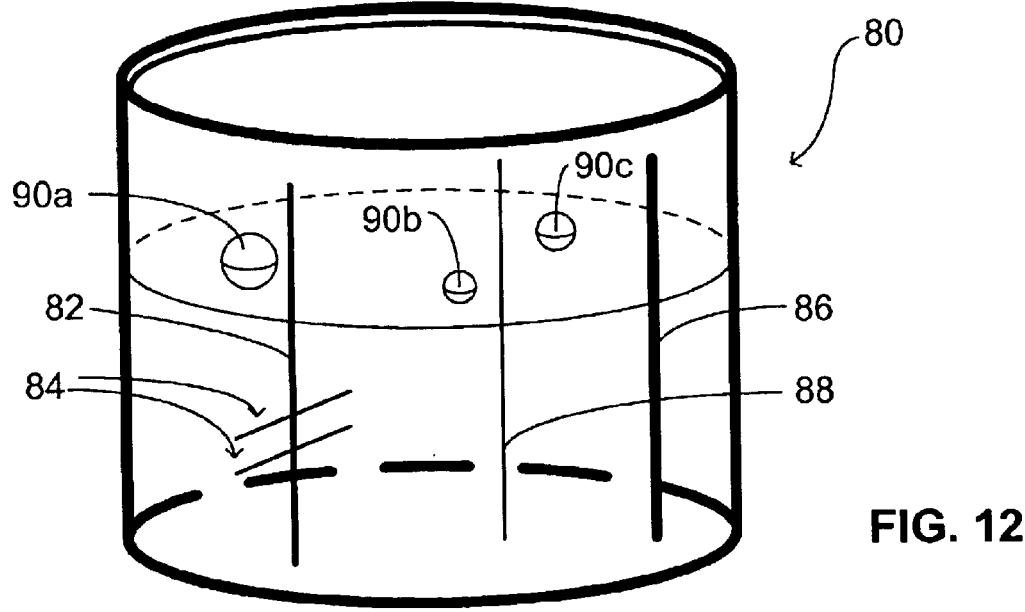
FIG. 12 is a perspective view of an embodiment of a completed lesion phantom of the invention with radiopaque objects.
Figure 13:
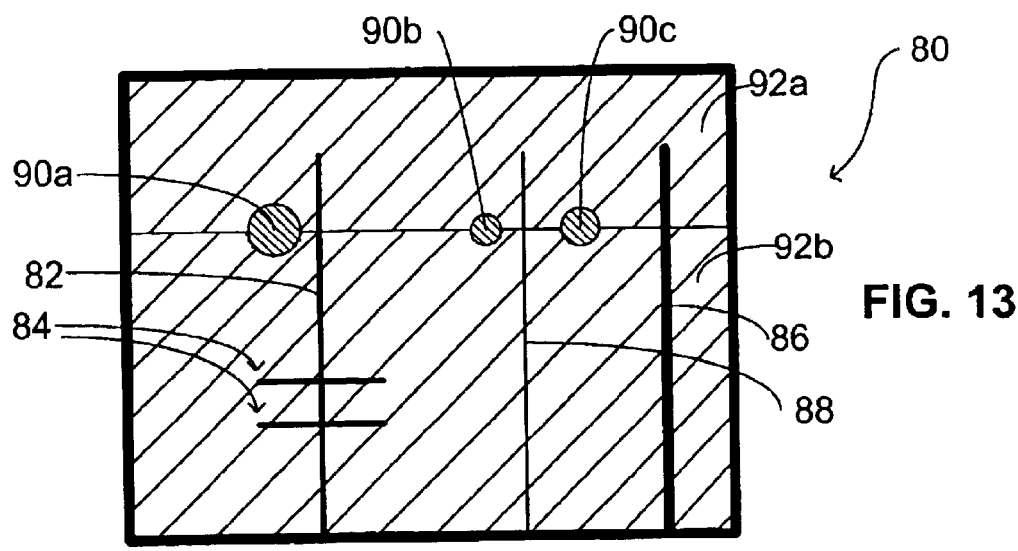
FIG. 13 is a cross sectional view of the lesion phantom of FIG. 12.

Turning to FIGS. 12 and 13, there are shown a perspective view and a cross-sectional view of an exemplary small animal lesion phantom 80 that includes radiopaque objects that mimic, for example, animal structures, such as a spine 82 and ribs 84, and rodlike structures 86 and 88 of different diameter that can be used to calibrate a scanner and/or measure the scanner's resolution. Lesion analogues 90a, 90b and 90c are placed in a volume of material 92 with a background level of radioactivity.

The lesion analogues utilized in the embodiments of the invention may vary in size from 0.1 mm$^3$ (or smaller) to 100 cm$^3$ (or larger), depending on the intended purpose of the particular phantom configuration. For example, present gamma camera have resolution of about 1 millimeter or less, and with advances, resolutions are regularly improving. Lesion analogue activity density relative to the background activity density may range from zero (a completely nonradioactive lesion analogue) to 100 times or more background activity density. A typical "hot-spot" phantom would have three to six lesion analogues varying in size from slightly smaller than the detector resolution limit to a size easily seen by the detector, with hot spot activity density being about ten times the background activity density. A typical "cold spot" or "defect" phantom would have three to six lesions varying in size from slightly smaller than the detector resolution limit to a size easily seen by the detector, with cold spot activity densities of, for example, 75%, 50%, 25% of background activity density, and a cold, or nonradioactive, lesion analogue. However, a smaller or greater number of lesion analogues can be provided.

The radionuclide used in the lesion analogues and used for the radioactive background can preferably be selected from known calibrators for the detector system the source is to be used with, or has radiation energies similar to radionuclides used with this detector system. These radionuclides include, but are not limited to Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95, with Ba-133, Co-57, Ge-68, Na-22, Gd-153, Cs-137 and Se-75 being particularly good nuclides. Furthermore, combinations of two or more radionuclides can be used.

Having thus described exemplary embodiments of the present invention, it should be understood by those skilled in the art that the above disclosures are exemplary only and, that various other alternatives, adaptations and modifications may be made within the scope of the present invention. The presently disclosed embodiments are to be considered in all respects as illustrative and not restrictive. The scope of the invention being indicated by the claims, rather than the foregoing description, and all changes which come within the meaning and range of equivalency of the claims are therefore intended to be embraced therein.

What is claimed is:

1. A lesion phantom with no inner cold encapsulation, comprising:
   at least one, three-dimensional, solid lesion analogue formed without any encapsulation by a dissimilar material; and
   a solid, three-dimensional background matrix into which at least one radionuclide is dispersed to form a background level of radioactivity, which background level of radioactivity is different than the level of radioactivity of the at least one lesion analogue, wherein the at least one, three-dimensional, solid lesion analogue is permanently and not removably positioned in the solid background matrix.

2. The lesion phantom of claim 1, wherein the at least one, three-dimensional, solid lesion analogue has a level of radioactivity higher than that of the solid background matrix.

3. The lesion phantom of claim 2, wherein the at least one, three-dimensional, solid lesion analogue has a radioactivity density relative to the background activity density ranging from slightly greater to about 100 times greater.

4. The lesion phantom of claim 1, wherein the at least one, three-dimensional, solid lesion analogue has a level of radioactivity lower than that of the solid background matrix.

5. The lesion phantom of claim 4, wherein the at least one, three-dimensional, solid lesion analogue has a radioactivity density relative to the background activity density that is completely non-radioactive to slightly less radioactive than the background activity density.

6. The lesion phantom of claim 1, wherein the at least one, three-dimensional, solid lesion analogue is formed from a material that has water- or tissue-equivalent density.

7. The lesion phantom of claim 1, wherein the at least one, three-dimensional, solid lesion analogue and the solid background matrix are formed from material selected from the group consisting of a resin, a urethane, a silicone, a polymer gel, a cement, and a castable ceramic.

8. The lesion phantom of claim 1, wherein the at least one, three-dimensional, solid lesion analogue has dispersed therethrough at least one radionuclide selected from the group consisting of Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95.

9. The lesion phantom of claim 1, wherein the at least one, three-dimensional, solid lesion analogue has dispersed therethrough at least one radionuclide selected from the group consisting of Ba-133, Co-57, Ge-68, Na-22, Gd-153, Cs-137 and Se-75.

10. The lesion phantom of claim 1, wherein the solid background matrix has dispersed therethrough at least one radionuclide selected from the group consisting of Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95.

11. The lesion phantom of claim 1, wherein the solid background matrix has dispersed therethrough at least one radionuclide selected from the group consisting of Ba-133, Co-57, Ge-68, Na-22, Gd-153, Cs-137 and Se-75.

12. The lesion phantom of claim 1, wherein the at least one solid lesion analogue is made into shapes ranging in sizes from about 0.1 mm$^3$ to about 100 cm$^3$.

13. The lesion phantom of claim 1, wherein the solid background matrix into which at least one radionuclide is dispersed is placed into a container.

14. The lesion phantom of claim 1, wherein the at least one, three-dimensional, solid lesion analogue without any encapsulation by a dissimilar material is imbedded into separately poured layers of the solid background matrix.

15. The lesion phantom of claim 1, wherein a plurality of the three-dimensional, solid lesion analogues are provided.

16. The lesion phantom of claim 15, wherein a plurality of the three-dimensional, solid lesion analogues are provided in a variety of sizes.

17. The lesion phantom of claim 1, further comprising at least one radiopaque object located in the solid background matrix.

18. A lesion phantom with no inner cold encapsulation, comprising:
a plurality of three-dimensional lesion analogues formed without any encapsulation by a dissimilar material, the lesion analogues comprising a matrix of solid material;
a container; and
a solid, three-dimensional background matrix into which at least one radionuclide is dispersed to form a background level of radioactivity, which background matrix is located in the container, wherein the background level of radioactivity of the background matrix is different than that of the level of radioactivity of the plurality of lesion analogues, and wherein the plurality of three-dimensional, solid lesion analogue are permanently positioned in the solid background matrix.

19. The lesion phantom of claim 18, wherein at least one of the plurality of three-dimensional lesion analogues has a level of radioactivity that is higher than that of the solid background matrix.

20. The lesion phantom of claim 18, wherein at least one of the plurality of three-dimensional lesion analogues has a level of radioactivity that is lower than that of the solid background matrix.

21. The lesion phantom of claim 18, wherein the plurality of three-dimensional lesion analogues have dispersed therethrough at least one radionuclide selected from the group consisting of Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95.

22. The lesion phantom of claim 18, wherein the plurality of three-dimensional lesion analogues have dispersed therethrough at least one radionuclide selected from the group consisting of Ba-133, Co-57, Ge-68, Na-22, Gd-153, Cs-137 and Se.

23. The lesion phantom of claim 18, wherein the solid background matrix has dispersed therethrough at least one radionuclide selected from the group consisting of Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95.

24. The lesion phantom of claim 18, wherein the solid background matrix has dispersed therethrough at least one radionuclide selected from the group consisting of Ba-133, Co-57, Ge-68, Na-22, Gd-153, Cs-137 and Se.

25. A method for manufacturing a lesion phantom with no inner cold encapsulation, comprising:
providing a container;
partially filling the container with a matrix material having a predetermined radioactivity level;
placing at least one solid, three-dimensional lesion analogue formed without any encapsulation into the container; and
placing additional matrix material in the container to encapsulate the at least one solid lesion analogue therein.

26. The method for manufacturing a lesion phantom with no inner cold encapsulation of claim 25, wherein in the step of partially filling the container with the matrix material, at least one recess sized to at least partially receive the at least one solid lesion analogue is formed in the matrix material, the at least one solid lesion analogue is placed in the recess, and then the container is filled with additional matrix material to encapsulate therein the at least one solid lesion analogue.

27. The method for manufacturing a lesion phantom with no inner cold encapsulation of claim 26, wherein the recesses is formed by molding.

28. The method for manufacturing a lesion phantom with no inner cold encapsulation of claim 25, wherein a plurality of different solid lesion analogues are encapsulated in the matrix.

29. The method for manufacturing a lesion phantom with no inner cold encapsulation of claim 25, further comprising the step of locating at least one radiopaque object in the container.

30. The method for manufacturing a lesion phantom with no inner cold encapsulation of claim 29, wherein the at least one radiopaque object has an anthropomorphic shape.

31. The method for manufacturing a lesion phantom with no inner cold encapsulation of claim 25, wherein the solid background matrix has dispersed therethrough at least one radionuclide selected from the group consisting of Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95.

32. The method for manufacturing a lesion phantom with no inner cold encapsulation of claim 25, wherein the plurality of three-dimensional solid lesion analogues have dispersed therethrough at least one radionuclide selected from the group consisting of Ag-110m, Am-241, Au-195, Ba-133, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95.

* * * * *